United States Patent [19]

Evans, Sr.

[11] 4,424,807
[45] Jan. 10, 1984

[54] PENILE IMPLANT

[76] Inventor: Alvin S. Evans, Sr., 234 Shubert Ave., Runnemede, N.J. 08078

[21] Appl. No.: 313,114

[22] Filed: Oct. 20, 1981

[51] Int. Cl.³ ............................................... A61F 5/00
[52] U.S. Cl. ....................................... 128/79; 128/344
[58] Field of Search ........................... 128/79, 344; 3/1

[56] References Cited

U.S. PATENT DOCUMENTS

| 4,009,711 | 3/1977 | Uson | 128/79 |
| 4,195,637 | 4/1980 | Gruntzig et al. | 128/348 |
| 4,235,227 | 11/1980 | Yamanaka | 128/79 |
| 4,318,396 | 3/1982 | Finney | 128/79 |

Primary Examiner—Dalton L. Truluck
Attorney, Agent, or Firm—Caesar, Rivise, Bernstein & Cohen, Ltd.

[57] ABSTRACT

A method of simulating a natural erection utilizing a penile implant which is arranged to be actuatable to simulate the natural erection. The implant comprises a pair of hollow, enclosed bladders, each formed of a membrane of thin, very flexible material and being capable of inflation from a flaccid state by the introduction of a fluid therein. Each bladder is located within a passageway formed in each corporus cavernosum. Means are provided for filling the bladders with fluid to inflate the bladders from the flaccid state to a predetermined volume without causing the bladder membrane to undergo tension. The predetermined volume is sufficiently great to cause the corpora cavernosa to expand so that its fibrous tissue envelope is stretched to encompass another predetermined volume, whereupon the fibrous tissue envelope becomes tense and the penis becomes hard and erect.

5 Claims, 6 Drawing Figures

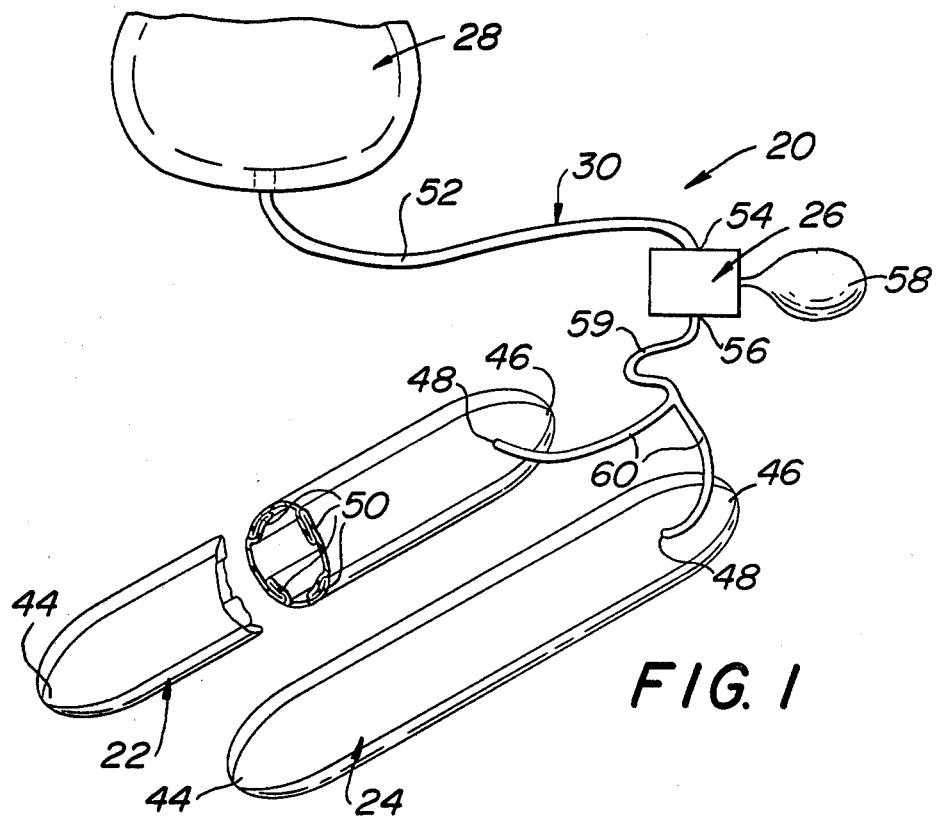
FIG. 1
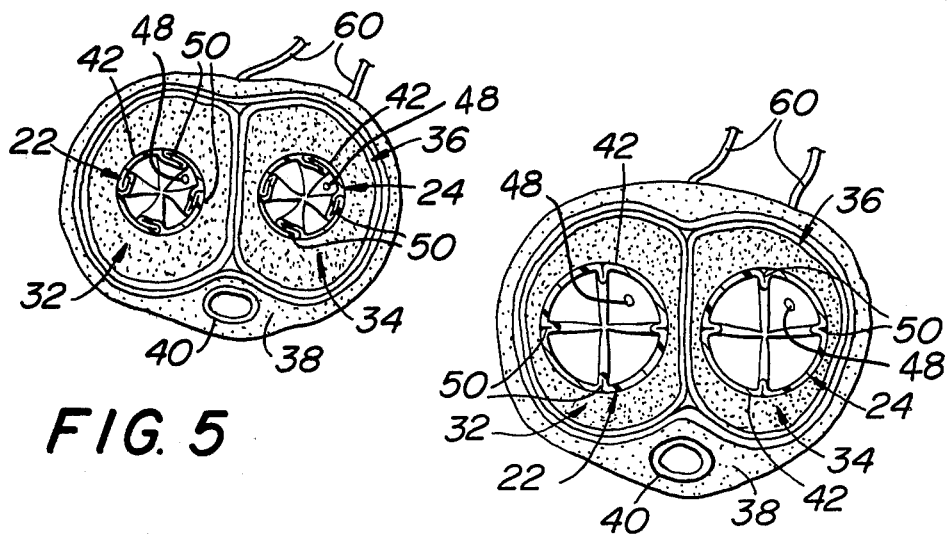
FIG. 5
FIG. 6

PENILE IMPLANT

BACKGROUND OF THE INVENTION

This invention relates generally to prosthetic devices and methods and more particularly to penile implants.

In order to remedy the effects of certain types of functional impotency, implants have been developed for surgical insertion in a penis to simulate a natural erection.

One of the first surgical implant techniques entailed the implanting of a solid, semi-rigid rod in each corpora cavernosa of the penis. While such a technique does result in the prevention of the penis from collapsing, thus permitting penetration during coitus, the technique suffers from various drawbacks. The most serious drawback of the semi rigid rod implant is that inasmuch as the rods as narrow, semi-rigid members, they do not increase the diameter or the length of the penis nor do they make the penis hard. Moreover, the solid rods are uncontrollable so that once surgically implanted, the penis is permanently extended.

In order to overcome the disadvantages of the solid rod technique a penile implant was developed utilizing a flexible elastic tube and a compressable container containing a fluid to be transferred from the container into the tube when the container is compressed so the fluid displaced into the tube elongates the tube and renders it relatively rigid. The tube is surgically implanted longitudinally along the penile shaft while the container is implanted in either the scrotum or in the abdominal cavity. An example of such a device is shown in U.S. Pat. No. 3,853,122 (Strauch, et al). While the Strauch, et al device appears to provide more functionality than the semi-rigid rods (since the Strauch device allows controlled actuation), the Strauch device does not appear capable of rendering the penis hard and enlarged.

Another implant device for effecting an erection is disclosed in U.S. Pat. No. 3,954,102 (Buuck). The Buuck prosthesis comprises a pair of expandable, resilient silicone rubber cylinders which are implanted in the corpora cavernosa to replace their function. A closed fluid supply is also implanted in the body and connected, via tubing, to the cylinders to inflate the cylinders and cause them to stretch, whereupon the diameter and length of the penis is increased. The fluid supply is in the form of an elastomeric bulb, which is squeezed through the person's skin to operate the device. Various valves are provided in the system so that the degree of the erection of the penis is controlled by varying the amount of fluid provided to the cylinders upon the squeezing of the bulb. Deflation of the cylinders is accomplished by actuating a bypass valve.

The implant disclosed in the Buuck patent appears to overcome various disadvantages of prior art techniques inasmuch as it not only prevents a penis from collapsing, but also enables the penis to become hard and enlarged upon actuation. However, inasmuch as the resilient cylinders are pressurized and expanded during the erection cycle of the device tensile stresses are produced in the material forming the cylinders. The repeated stresses of actual operation result in the eventual rupture of the cylinders, thus requiring surgical replacement.

Other expandable cylinder-type penile implants have been disclosed in the patent literature, such as disclosed in U.S. Pat. No. 4,009,711 (Uson). The Uson device, like other resilient, expandable cylinder implant devices has the tendency to fail or rupture due to the stresses engendered during repeated inflation and deflation.

OBJECTS OF THE INVENTION

Accordingly, it is a general object of the instant invention to provide a penile implant and method of simulating a natural erection which overcomes the disadvantages of the prior art.

It is another object of the instant invention to provide a method of simulating a natural erection utilizing a penile implant which is simple in construction and suitable for long term repeated operation.

It is a further object of this invention to provide a method of simulating a natural erection utilizing a penile implant which is resistant to failure resulting from repeated long term use.

SUMMARY OF THE INVENTION

These and other objects of the instant invention are achieved by providing a prosthetic device for implantation in a penis to simulate a natural erection when the device is actuated. The penis comprises corpora cavernosa bounded by an envelope of fibrous tissue expandable to a predetermined maximum size at which point the tissue becomes tense. The envelope of the fibrous tissue bounding the corpora cavernosa encompasses a first predetermined volume when the penis is flaccid. The corpora cavernosa is capable of expansion so that the envelope encompasses a second predetermined volume, with the limit of expansion of the corpora cavernosa being the second predetermined volume and being established by the maximum expansion of the fibrous tissue. Each of the corporus cavernosum have a passageway formed therein. The device comprises a pair of hollow, enclosed bladders, each having an access port to the interior thereof and formed of a membrane of thin, very flexible material. Each of said bladders is capable of inflation by the introduction of a fluid therein through its port. A respective one of the bladders is located in the passageway in each corporus cavernosum. Means are coupled to the ports for filling the bladders with the fluid to inflate the bladders from their flaccid state to a third predetermined volume without causing the bladder membrane to undergo tension. The third predetermined volume is sufficiently great to cause the corpora cavernosa to expand so that the fibrous tissue envelope encompasses the second predetermined volume, whereupon the fibrous tissue becomes tense and the penis becomes erect and hard.

Other objects and many of the attendant advantages of the instant invention will be readily appreciated by reference to the following detailed description when considered in connection with the accompanying drawing, wherein:

DESCRIPTION OF DRAWINGS

FIG. 1 is a respective view of the prosthetic device of the instant invention;

FIG. 5 is a sectional view taken along line 5—5 of FIG. 3; and,

FIG. 6 is an enlarged sectional view taken along line 6—6 of FIG. 4.

DETAILED DESCRIPTION OF THE PREFERRED EMBODIMENT

Figure 2:
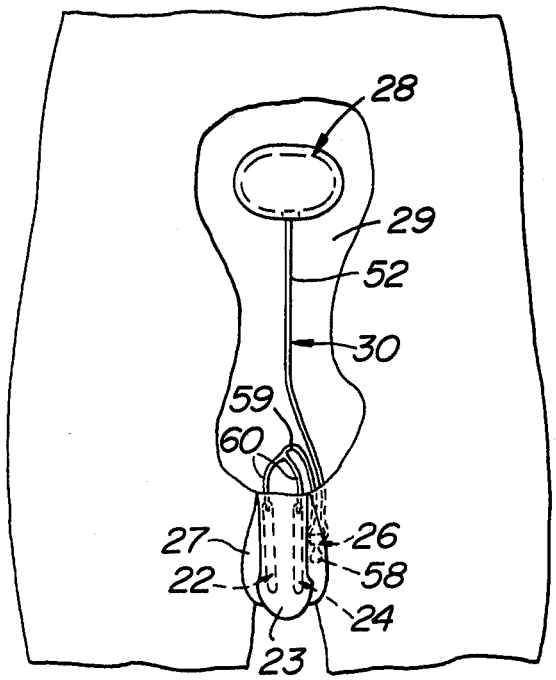
FIG. 2 is a front elevational view, partially broken away, of the human anatomy of a male's crotch area showing the prosthetic device implanted in a typical arrangement.

Referring now to the various figures of the drawing wherein like reference characters refer to like parts there is shown at 20 the prosthetic device which is utilized in accordance with the method of obtaining a simulated erection as set forth in the instant invention.

The device 20 basically comprises a pair of bladders 22 and 24, a valve and pump assembly 26, a fluid reservoir 28, and intercommunicating flexible conduits 30. The entire device 20 is arranged to be surgically implanted in the body, with the two bladders 22 and 24 being disposed within the penis 23, with the combination valve and pump assembly 26 (disposed in either the abdominal cavity or in the scrotum 25 (as shown) and with the reservoir 28 disposed with the abdominal cavity 27.

In order to best understand the operation of the device in effecting the simulation of a natural erection, a brief review of the physiology of the portions of the penis relevant to the instant invention will be discussed hereinafter. To that end basically the penis 23 comprises a pair of corpora cavernosa 32 and 34 which extend the length of the penile shaft. The corpora cavernosa are surrounded by an envelope of fibrous tissue 36. The corpus spongiosum 38 extends along the penile shaft under the corpora cavernosa, with the urethra 40 passing therethough.

Each corpora cavernosum encompasses a predetermined minimal volume within the envelope 36 when the penis is flaccid. In a functional penis, the engorgement of the spongy tissue of the corpus cavernosum with blood results in its expansion to be a maximum or "erect" volume. The maximum volume is established by the action of the fibrous tissue envelope surrounding the corpous cavernosum stretching to its maximum, whereupon that tissue becomes tense with the engorged corpus cavernosum constrained therein so that the penis is now elongated, enlarged, hard and erect.

The bladders 22 and 24 of the instant invention are arranged for surgical implantation in respective corpus cavernosum and are constructed to mechanically expand the corpora cavernosa until the fibrous tissue envelope 36 becomes tense, thereby producing a functional erection without the neccessity for the corpora cavernosa to be engorged with blood. The bladders are readily deflatable to enable the penis to become flaccid when an erection is no longer sought. The mechanical expansion/contraction action of the bladders is capable of a large number of operational cycles without bladder failure due to the fact that the bladders' physical construction insures that the material forming the bladders' membrane does not undergo tension in producing the erection, as has characterized prior art inflatable penile implants.

The bladders 22 and 24 are placed within the respective corpora cavernosum by surgically preparing a passageway 42 therein. The passageway 42 can be formed by any conventional surgical technique used for prior art penile implants, such as that disclosed in the heretofore mentioned Buuck patent. In FIGS. 5 and 6, the passageways 42 are shown as being of circular cross-section. That shaped passageway is merely exemplary. Thus, it is to be understood that the passageways can be of any suitable shape. Each passageway 42 extends down a substantial portion of the length of the associated corporus cavernosum from a point adjacent the glans penis to a point adjacent the scrotum.

Each of the bladders of the instant invention is an enclosed hollow member formed of a very thin, e.g., 2-5 mils, flexible membrane. One particularly suitable material for forming the membrane is silicone rubber. As can be seen clearly in FIG. 1, each bladder is of generally cylindrical shape whose opposed ends are rounded or domed. The front end of the bladder is denoted by the reference numeral 44 and the rear end by reference numeral 46. The front end 44 is arranged to be located adjacent the glans penis when the bladder is located within the passageway 42 and with the rear end 46 located adjacent the root of the penile shaft close to the scrotum. Each bladder includes an opening or access port 48 to the interior thereof and which is located adjacent the rear end 46 of the bladder.

The bladders are arranged to be filled with a fluid, such as water, through its respective access port 48 to cause the bladder to expand longitudinally, as well as radially. Since each bladder is located in a respective passageway 42 in a corpora cavernosa, the expansion of the bladder causes concomitant expansion of the corpora cavernosa from its minimal volume (its "flaccid volume") to an increased volume.

Figures 3, 4:
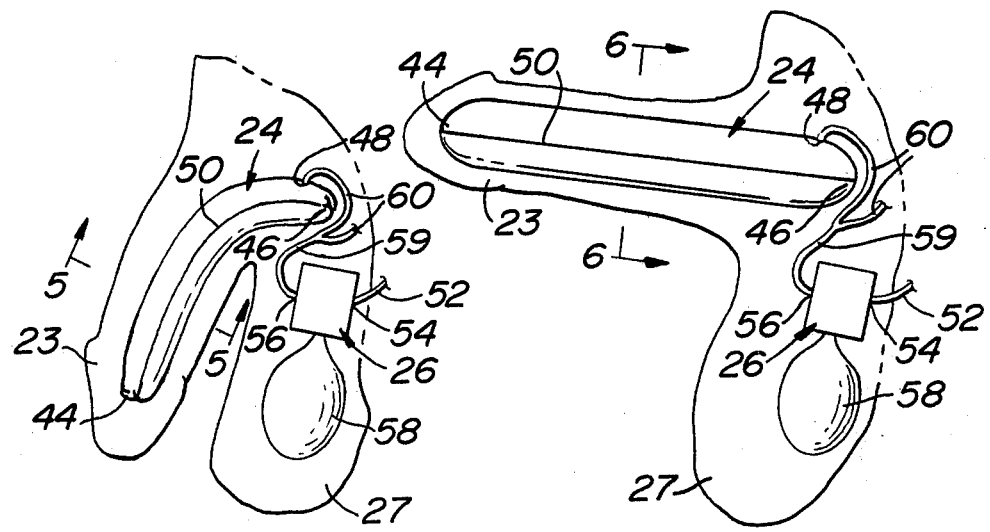
FIG. 3 is a side elevational view of the genital area of a male and showing a portion of the device of the instant invention implanted therein and with the penis being in a flaccid state.
FIG. 4 is a side elevational view, similar to that of FIG. 3, but showing the device in operation to cause the penis to be erect and hard.

In accordance with a primary aspect of the invention each bladder has sufficient volumetric capacity so that when it is inflated to the condition where the fibrous envelope 36 surrounding the corpora cavernosa has reached the limit of its expansion, the material forming the membrane wall of the bladder has not reached the point at which it undergoes tension, e.g., it does not begin to stretch. To achieve that characteristic, each bladder includes plural folded or overlapped portions 50 (FIGS. 5 and 6), that is portions which overlie each other when the bladder is in less than its maximum volume state. Moreover, the length of each bladder is selected so that when it is in position in its associated passageway 42 in a flaccid penis, the ends 44 and 46 of the bladder are folded up, with portions of the bladder membrane overlying each other as shown in FIG. 3. The overlying or folded portions 50 of the bladder membrane, as well as the folded ends of the bladder membrane, enable the bladder to fill the surgical passageway 42 when the corpus cavernosum is flaccid, yet provide the bladder with sufficient reserve fluid-holding capacity so that it can be inflated (i.e., filled) to the state at which it expands and lengthens the corpus cavernosum and stretches the surrounding fibrous tissue 36 to the tension point of the fibrous tissue (so that the penis is rendered elongated, enlarged, erect and hard) without the bladder membrane material undergoing tension.

In FIG. 5 there is shown the bladders 22 and 24 in a partially filled or "flaccid") state in a flaccid penis, whereas in FIG. 6 the bladders are shown in their "maximum" volumetric state so that the penis is erect. As can be seen in FIG. 6, there are still some overlying folds 50 in the bladder membrane even though the fibrous tissue 36 has been expanded to its maximum, thereby precluding any further expansion of the bladders. In addition, there are still some overlying folds at each end of the bladders. These folds have been omitted from FIG. 6 in the interest of drawing simplicity.

In accordance with a preferred embodiment of this invention, the bladders 22 and 24 are preferably dimensioned to have additional reserve volumetric capacity (e.g., 20-25% greater) beyond that necessary to effect an erection of the penis, as shown in FIG. 6 and before all of the folds are taken up by the bladders' expansion.

It must be pointed out at this juncture that while the overlapped or folded portions 50 of the bladder membrane are shown as extending longitudinally the length of the bladder and being disposed in an equadistantly spaced array about the periphery of the cylindrical bladder, such a construction is only one of many possible arrangements and is thus merely exemplary. Thus, the folded or overlying portions 50 of the membrane can be randomly located at any locations on the periphery and along the length of the bladder. Moreover, the folds or overlying portions need not be permanently formed in the membrane making up the bladder's wall. For example, a smooth walled oversized bladder can be used since such a bladder will inherently fold up forming random flaps and folds 50 when it is placed within the passageway 42 in the corpora cavernosa. Thus, in accordance with the instant invention all that is required is that the bladder have sufficient volumetric capacity above its partially filled state so that when filled to the state at which it causes the surrounding corpora cavernosa to expand the fibrous tissue envelope to the point at which further stretching ceases (and the envelope becomes tense and the penis erect), the walls of the bladder membrane do not undergo tension, nor do they stretch.

The means for filling the bladders 22 and 24 comprises the reservoir 28, the valve pump assembly 26 and the interconnecting tubing or conduits 30. To that end, the reservoir 28 is connected, via a tubing section 52, to one port 54 of the valve-pump assembly 26. The valve-pump assembly 26 comprises a squeezable bulb 58 coupled to interiorly located valves (not shown). The valve-pump assembly 26 also includes a second port 56 to which a Y-shaped conduit section is connected. The common leg 59 of the Y-shaped conduit section is connected to the port 56, whereas each leg 60 of the conduit section is connected to a respective access port 48 of the bladders 22 and 24.

As mentioned heretofore, the reservoir is surgically located within the abdomen while the valve-pump assembly is located within the scrotum.

Operation of the device to produce an erection is as follows: The bulb 58 is squeezed through the skin of the scrotum, whereupon water from the reservoir 28 is forced through the port 56 and the Y tubing 59 to the associated access ports 48 of each of the bladders. Thus, the bladders begin to fill beyond the partially filled state shown in FIG. 5. The pump bulb 58 has to be squeezed several times to effect a full erection. In this regard, each time that the pump bulb is squeezed, more water is forced into the bladders through the Y conduit. Release of the pump or bulb 58 does not allow the water to return to the reservoir since the valve in the valve-pump assembly 26 is of the one-way type. Thus, each time the bulk is resqueezed, additional water is forced into the bladders. This action causes the bladders to expand from the condition shown in FIG. 5 to the fully filled or erect condition shown in FIG. 6. In order to effect the filling of the bladders, all that is required is pressure on the order of 2½ psi. The bladders remain in their fully filled state so that the erection is maintained so long as the water in the bladders is precluded by the valve from flowing back to the reservoir. When it is desired to render the penis flaccid, all that is required is to actuate a release mechanism (not shown) forming a portion of the valve-pump assembly 26 by squeezing on the scrotum where the release mechanism is located, whereupon the valve in the assembly 26 enables the water to flow out of the bladder and into the reservoir under the natural pressure caused by the resiliency of the fibrous envelope 36 on the bladders. When the pressure produced on the water in the bladders by fibrous tissue envelope 36 equals the pressure on the water in the reservoir, the flow of water ceases. Thus, the pump bulb 58 must be squeezed to force the water back into the reservoir so that the bladders are back in their partially deflated condition shown in FIG. 5, whereupon the penis is limp and flaccid.

The reservoir 28 may be constructed by any suitable construction, e.g., such as taught in the Buuck U.S. Pat. No. 3,954,102. The valve-pump assembly 26 is preferably constructed in accordance with the teachings of my co-pending U.S. patent application Ser. No. 366,447, filed on Apr. 7, 1982, and entitled Pump and Valve Assembly for Penile Implant, and whose disclosure is incorporate by reference herein. However, other combined valve-pump assemblies or individual valve and pump components, such as also disclosed in the Buuck patent and in other prior art patents, may be used, if desired.

It should be appreciated from the foregoing, that by providing a bladder whose volumetric capacity is sufficiently great to insure that the fibrous envelope surrounding the corpora cavernosa undergoes tension without the bladder undergoing tension, the risk of bladder failue due to fatigue under repeated stress is minimized, if not eliminated.

It must be pointed out at this juncture that while the device is shown as being formed of a membrane of silicone rubber, other resilient materials can be used as well. In fact, inasmuch at the bladder is arranged so that it does not undergo any tension (and is thus not meant to stretch), non-resilient, flexible materials may also be utilized. Examples of such materials are nylon, acrylon, etc. Thus, all that is required of the material is that it be strong, flexible, capable of holding water or other liquids therein and suitable for implantation in human tissue.

As will be appreciated from the foregoing, the device of the instant invention is simple in construction yet provides a sure and effective device for producing an erection having all the attributes of a functional erection and which device is suitable for long term, repeated reliable operation.

Without further elaboration the foregoing will so fully illustrate my invention that others may, by applying current or future knowledge, readily adapt the same for use under various conditions of service.

What is claimed as the invention is:

1. A method of simulating a natural erection in a penis having coprora cavernvosa bounded by an envelope of fibrous tissue expandable to a predetermined maximum size, whereupon said envelope encompasses a first predetermined volume when said penis is flaccid, said corpora cavernvosa being expandable wherein said envelope encompasses a second predetermined volume when said penis is hard and erect, with the limit of said expansion of said corpora cavernosa being said second predetermined volume and being established by the maximum expansion of said fibrous tissue, each of said corpus cavernvosum having a passageway formed therein, said method comprising the steps of:

(1) implanting in the passageway of each corpus cavernvosum a hollow, enclosed bladder, each bladder having an access port in communication with the interior thereof and formed of a membrane of thin, flexible material, (2) connecting said access ports to a source of fluid, (3) directing fluid through said access ports from said fluid source to said bladders to inflate said bladders from said flaccid state to a third predetermined volume, said third predetermined volume being less than the maximum volumetric capacity of said bladders so as not cause the respective bladder membranes to undergo tension, while being sufficiently great to cause said corpora cavernosa to expand so that said fibrous tissue encompasses said second predetermined volume to cause said fibrous tissue to become tense and said penis to become erect and hard.

2. The method of claim 1, wherein portions of said bladder membrane are lapped and overlie each other when said bladder is in a flaccid state.

3. The method of claim 1, wherein flexible conduit means are utilized in connecting said fluid source to said access ports.

4. The method of claim 3, wherein the passage of fluid from said fluid source to said access ports is controlled by valve means.

5. The method of claim 4, wherein said valve means is remotely located from said bladders.

* * * * *